United States Patent
Thompson et al.

(10) Patent No.: US 7,209,790 B2
(45) Date of Patent: Apr. 24, 2007

(54) MULTI-MODE PROGRAMMER FOR MEDICAL DEVICE COMMUNICATION

(75) Inventors: David L. Thompson, Andover, MN (US); Koen J. Weijand, Alfas Del Pi (ES); Daniel R. Greeninger, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 447 days.

(21) Appl. No.: 10/722,891

(22) Filed: Nov. 26, 2003

(65) Prior Publication Data

US 2004/0167587 A1  Aug. 26, 2004

Related U.S. Application Data

(63) Continuation-in-part of application No. 10/261,317, filed on Sep. 30, 2002.

(51) Int. Cl.
*A61N 1/08* (2006.01)

(52) U.S. Cl. .......................... 607/60; 128/903

(58) Field of Classification Search ................ 128/903; 607/30–32, 59, 60
See application file for complete search history.

(56) References Cited

U.S. PATENT DOCUMENTS

| | | | |
|---|---|---|---|
| 3,857,399 A | 12/1974 | Zacouto | 128/419 |
| 4,556,063 A | 12/1985 | Thompson et al. | 128/419 PT |
| 4,821,724 A | 4/1989 | Whigham et al. | 128/419 |
| 5,113,869 A | 5/1992 | Nappholz et al. | 128/696 |
| 5,127,404 A | 7/1992 | Wyborny et al. | 128/419 P |
| 5,213,098 A | 5/1993 | Bennett et al. | 128/419 |
| 5,345,362 A | 9/1994 | Winkler | 361/681 |
| 5,354,319 A | 10/1994 | Wyborny et al. | 607/32 |
| 5,383,915 A * | 1/1995 | Adams | 607/60 |
| D358,583 S | 5/1995 | Winkler | D14/106 |
| 5,417,717 A | 5/1995 | Salo et al. | 607/18 |
| 5,466,246 A * | 11/1995 | Silvian | 607/32 |
| 5,626,630 A | 5/1997 | Markowitz et al. | 607/60 |
| 5,752,976 A | 5/1998 | Duffin et al. | 607/32 |
| 5,772,586 A | 6/1998 | Heinonen et al. | 600/300 |
| 5,836,975 A | 11/1998 | DeGroot | 607/5 |
| 5,948,006 A * | 9/1999 | Mann | 607/61 |
| 5,987,356 A | 11/1999 | DeGroot | 607/5 |
| 5,999,857 A * | 12/1999 | Weijand et al. | 607/60 |
| 6,078,837 A * | 6/2000 | Peterson et al. | 607/14 |
| 6,083,248 A | 7/2000 | Thompson | 607/30 |

(Continued)

OTHER PUBLICATIONS

Texas Instrument—Product Folder—TMS320C242—16-bit, 5V Fixed-Point DSP, first item on the page, Sep. 3, 2006.*

(Continued)

*Primary Examiner*—Robert E. Pezzuto
*Assistant Examiner*—Frances P. Oropeza
(74) *Attorney, Agent, or Firm*—Daniel G. Chapik; Girma Wolde-Michael

(57) ABSTRACT

The invention is directed to a programmer for communication with different medical devices that utilize different telemetry communication techniques. The programmer receives telemetry signals from a given medical device, and selects an appropriate communication mode, which can be pre-programmed into the programmer as one of a plurality of possible communication modes. The programmer can configure itself for communication with a given medical device based on the telemetry signal it receives. Specifically the programmer is implemented as a software based, power efficient receiver/transmitter based upon an inexpensive, simple motor-controller DSP.

16 Claims, 11 Drawing Sheets

U.S. PATENT DOCUMENTS

| | | | |
|---|---|---|---|
| D438,204 S | 2/2001 | Winkler | D14/356 |
| 6,200,265 B1 | 3/2001 | Walsh et al. | 600/300 |
| 6,292,698 B1 | 9/2001 | Duffin et al. | 607/32 |
| 6,298,271 B1 * | 10/2001 | Weijand | 607/60 |
| 6,443,891 B1 | 8/2002 | Grevious | 600/302 |
| 6,482,154 B1 | 11/2002 | Haubrich et al. | 600/300 |
| 6,802,811 B1 * | 10/2004 | Slepian | 600/309 |
| 2002/0082665 A1 | 6/2002 | Haller et al. | 608/60 |

OTHER PUBLICATIONS

Forney, R.C., et al., *Activation Times for "Emergency Backup" Programs*, PACE, vol. 19, Apr. 1996, Part I, p. 465-471.

Stirbys, *A Challenge: Development of a Universal Programmer*, PACE, vol. 16, Apr. 1993, Part I, p. 693-4.

* cited by examiner

MULTI-MODE PROGRAMMER FOR MEDICAL DEVICE COMMUNICATION

RELATED APPLICATIONS

This application is a continuation in part of Ser. No. 10/261,317, filed on Sep. 30, 2002.

FIELD OF THE INVENTION

The invention relates to medical devices, particularly, medical devices equipped to communicate via telemetry. More particularly, the invention relates to a device and method for transmitting and receiving telemetry signals from an implantable medical device with a simple, energy efficient, and inexpensive motor controller DSP. Further, the invention relates to a universal programmer/interrogator/activator for implantable medical devices from several manufacturers.

BACKGROUND

Telemetry generally refers to communication of data, instructions, and the like between a medical device and a medical device programmer. For example, the programmer may use telemetry to program a medical device to deliver a particular therapy to a patient. In addition, the programmer may use telemetry to interrogate the medical device. In particular, the programmer may obtain diagnostic data, event marker data, activity data and other data collected or identified by the medical device. The data may be used to program the medical device for delivery of new or modified therapies. In this manner, telemetry between a medical device and a programmer can be used to improve or enhance medical device therapy.

Telemetry typically involves wireless data transfer between a medical device and the programmer using radio frequency (RF) signals, infrared (IR) frequency signals, or other electromagnetic signals. Any of a variety of modulation techniques may be used to modulate data on a respective electromagnetic carrier wave. Alternatively, telemetry may be performed using wired connections, sound waves, or even the patient's flesh as the transmission medium. A number of different telemetry systems and techniques have been developed to facilitate the transfer of data between a medical device and the associated programmer.

Many implantable medical devices (IMDs) support telemetry. Examples of an IMD include implantable cardiac pacemakers, implantable defibrillators, implantable pacemaker/cardioverter/defibrillators, implantable muscular stimulus devices, implantable brain stimulators, other implantable organ stimulation devices, implantable drug delivery devices, implantable monitors, and the like. Telemetry, however, is not limited to communication with IMDs. For example, telemetry may also be used to communicate with non-implanted medical devices in substantially the same way as it is used with IMDs.

The evolution and advancement of telemetry has yielded a number of advances in the art including, for example, improved communication integrity, improved data transmission rates, improved communication security, and the like. Moreover, as new therapeutic techniques are developed, telemetry allows the new techniques to be programmed into older medical devices, including devices previously implanted in a patient. Unfortunately, the evolution of telemetry has also resulted in proliferation of a wide variety of different systems and communication techniques that generally require a unique programmer for communication with each type of device. Consequently, different types of medical devices, medical devices manufactured by different companies, or even similar medical devices manufactured by the same company, often employ different telemetry techniques. Accordingly, a wide variety of different programmers are needed to communicate with different medical devices in accordance with the different telemetry techniques employed by the medical devices.

A proposed solution to the large and diverse number of programmers required in a hospital and/or follow-up clinic environment to program, interrogate or follow patients with IMDs is a "universal programmer" as proposed, for example, by P Stirbys in "A Challenge: Development of a Universal Programmer", PACE, Vol. 16, April 1993, pg 693–4 and by R Fortney, et al in "Activation Times for "Emergency Backup" Programs", PACE, Vol. 19, April 1996, pg 465–71. As pointed out in these articles, the difficulty of implementing the required multiple up/down link formats for even a subset of the programmers currently in use and applying all the various formats in a single programmer is formidable.

Prior art programmers have included optimized and customized bandpass filters and demodulators for demodulating and detecting the telemetered data signal from an IMD from a particular manufacturer. It would be prohibitively expensive, large and complex to incorporate the required amplification, filtering and demodulation of all manufacturers' IMDs in a single programmer.

Although such typical present day programmers have performed generally effectively, they are considered to be unduly complex and bulky, requiring a lot of shelf space to store programmers from several manufacturers in a typical clinic. There is a need for an energy efficient programmer apparatus of this kind that is configurable to receive and demodulate data telemetered from a variety of implantable devices according to many different modulation schemes, with reduced complexity, size and cost. The present invention fulfills this need.

SUMMARY

In general, the invention is directed to a multi-mode programmer for communication with different medical devices that utilize different telemetry communication techniques. The programmer receives telemetry signals from a given medical device, and selects an appropriate communication mode, which can be pre-programmed into the programmer as one of a plurality of possible communication modes. For example, upon receiving a telemetry signal from the medial device, the programmer may identify a signature associated with the received telemetry signal. The programmer can then select the appropriate communication mode, such as by accessing a lookup table that associates signatures with communication modes. Accordingly, the programmer can selectively configure itself for communication with a given medical device based on the telemetry signal it receives from that medical device.

In one embodiment, the invention provides a method comprising receiving a first signal from a medical device, and selecting a communication mode from a plurality of possible communication modes based on the first signal. For example, selecting the communication mode based on the first signal may include identifying a signature that substantially correlates to the first signal, and selecting a communication mode associated with the signature.

In another embodiment, the invention provides a programmer for a plurality of different medical devices. The programmer may include memory to store a plurality of possible communication modes for the programmer, and a control unit to receive a first signal from a medical device and select a communication mode from the plurality of possible communication modes based on the first signal.

The invention provides various advances in the art. In particular, the invention can eliminate the need for multiple programmers for telemetric communication with different medical devices. Instead, a multi-mode programmer can be used to communicate with a plurality of different medical devices on a selective basis. In addition, the invention may find useful application as an interrogator in emergency (first responder and emergency room) scenarios by facilitating the ability to identify and communicate with medical devices used by a given patient. In that case, the ability to obtain diagnostic and therapeutic information from a given medical device without requiring knowledge of the make and model of the device may save valuable time, possibly saving lives. In this embodiment, the programming of parameters may not be available, which may further reduce device size and complexity.

The invention may also provide distinct advances in the art in terms of the size (form factor) and mechanical configuration of a programmer, useful for patient activation/control. For example, a number of mechanical configurations are envisioned, including wearable configurations such as configurations similar to jewelry, a wristwatch or a belt buckle to be worn by the patient or medical personnel. In addition, a programmer in the form of an ID card or adhesive patch with a removable memory card are envisioned for use by a patient so that information can be collected on the removable memory card when the patch is adhered to the patients skin. In that case, the memory card may be removed from the programmer and sent it to a physician for analysis without the need to send the entire programmer to the physician. Accordingly, the programmer can be reused with another memory card. Of course, the programmer itself could also be sent by the patient to the physician, in accordance with other embodiments. These and other unique wearable configurations can be realized in various embodiments of the invention, some of which may have dimensions less than approximately 60 millimeters by 90 millimeters by 15 millimeters, i.e., a form factor similar to that of a thick credit card.

The present invention is embodied in an apparatus and method for receiving a data signal telemetered from an implantable device and modulated by digital data according to any of a number of distinct modulation modes. The apparatus includes an antenna system, a front-end receiver for receiving and amplifying the modulated data signal and an analog-to-digital converter for sampling the amplified signal to produce a sequence of digitized samples. In addition, a digital signal processor is included for implementing a plurality of bandpass filters and plurality of demodulators, including an amplitude demodulator, a frequency demodulator, and a phase demodulator. Further, the digital signal processor filters the sequence of digitized samples using a selected one of the plurality of bandpass filters and then demodulates the filtered sequence of samples using a selected one of the plurality of demodulators. A demodulated signal thereby is produced without the need for unnecessarily duplicative hardware filters and demodulators.

In a more detailed feature of the invention, the front-end receiver includes an antenna system for receiving the modulated data signal via electromagnetic radiation. The apparatus further may include a transmitter for transmitting a data signal via the antenna system to the implantable device.

In an additional feature of the invention, the digital signal processor may include several methods and processes to reduce energy requirements during operation to allow battery operation.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

DETAILED DESCRIPTION

Figure 1:
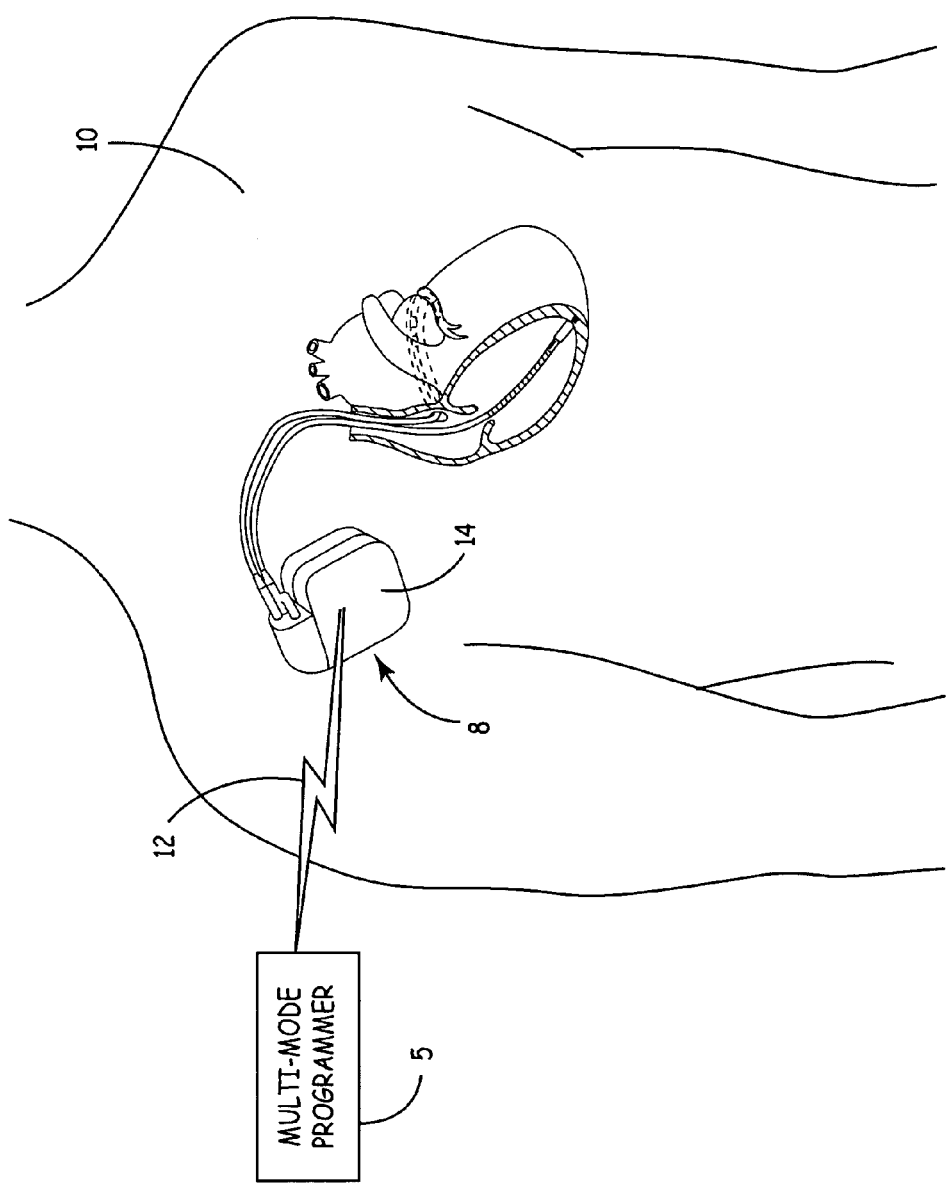
FIG. 1 is a conceptual diagram illustrating a multi-mode programmer communicating with an exemplary medical device implanted in a human body.

FIG. 1 is a conceptual diagram illustrating a multi-mode programmer 5 communicating with an exemplary medical device 8 implanted in a human body 10. Medical device 8 represents one of a variety of medical devices that may communicate with programmer 5. Although illustrated as an implantable cardiac pacemaker, medical device 8 may take the form of a variety of other medical devices such as, for example, an implantable defibrillator, an implantable pacemaker/cardioverter/defibrillator, an implantable muscular stimulus device, an implantable brain stimulator, an implantable nerve stimulator, an implantable drug delivery device, implantable monitor, or the like. In addition, medial device 8, as described herein, is not necessarily limited to an implantable device. Also, in some cases, medical device 8 may correspond to a medical device used on non-human mammals or other animals. In short, the techniques described herein may be readily used with a wide variety of medical devices including implanted and non-implanted medical devices used to deliver therapy or perform diagnosis in humans, mammals, or other types of living beings.

In the example shown in FIG. 1, medical device 8 includes a hermetically sealed enclosure 14 that may include various elements, although the invention is not limited to hermetically sealed devices. By way of example, enclosure 14 may house an electrochemical cell, e.g., a lithium battery, circuitry that controls device operations and records sensed events, physiological activity and patient conditions, and a control unit coupled to an antenna to transmit and receive information via wireless telemetry signals 12.

Programmer 5 communicates with medical device 8 via telemetry signals 12. For example, programmer 5 may use telemetry signals 12 to program medical device 8 to deliver a particular therapy to human body 10, such as electrical stimulation, drug administration or the like. In addition, medical device 8 may use telemetry signals 12 to send information to programmer 5 such as diagnostic information, sensed conditions associated with the patient, information relating to therapy delivered to the patient, or any other information collected or identified by medical device 8. In this manner, telemetry allows communication between medical device 8 and programmer 5.

In accordance with the invention, programmer 5 supports communication via a number of different telemetry modes. Accordingly, programmer 5 is capable of receiving and interpreting telemetry signals sent by medical devices that use different types of telemetry. Moreover, programmer 5 can communicate to different medical devices using selected communication modes that correspond to the given medical device with which programmer 5 is currently communicating. The different telemetry modes of programmer 5 may cause programmer 5 to select different telemetry techniques. For example, programmer 5 may be equipped to detect characteristic features of signals sent to programmer 5 via different communication modes, such as unique carrier waveform shapes, amplitudes, frequency and/or timing of the modulated waveform, or the like. Based on the detected characteristics, programmer 5 selects one of the telemetry modes appropriate for communication with medical device 8.

Programmer 5 may be embodied in a wide variety of mechanical configurations. By way of example, programmer 5 may comprise a device worn on a patient's wrist, much like a wrist watch, and may even comprise a fully functional wrist watch that tells time, but also includes the programmer functionality described herein. Alternatively, programmer 5 may be worn around a patient's neck, like a necklace, or around a patient's waist, like a belt. In other configurations, programmer 5 may be embodied in an identification card, a pendent, a laptop computer, a handheld computer, a pager, or the like. In some cases, programmer 5 may comprise a programmed computer used by emergency medical personnel, e.g., in an ambulance, to communicate with a variety of possible medical devices that may be implanted within a given patient. In still other cases, programmer 5 may be embodied as an adhesive patch that is adhered to a patient's skin. These and other configurations of programmer 5 may be used in accordance with the invention.

In any case, programmer 5 receives telemetry signals 12 from a given medical device 8, and dynamically selects an appropriate communication mode, which can be pre-programmed into programmer 5 as one of a plurality of possible communication modes. For example, upon receiving a telemetry signal 12 from medical device 8, programmer 5 may identify a signature associated with the telemetry signal 12. Programmer 5 may then select the appropriate communication mode, such as by accessing a lookup table (LUT) that associates signatures with communication modes. Then, the programmer 5 can configure itself for communication with medical device 8 based on the telemetry signal 12 received from medical device 8.

Figure 2:
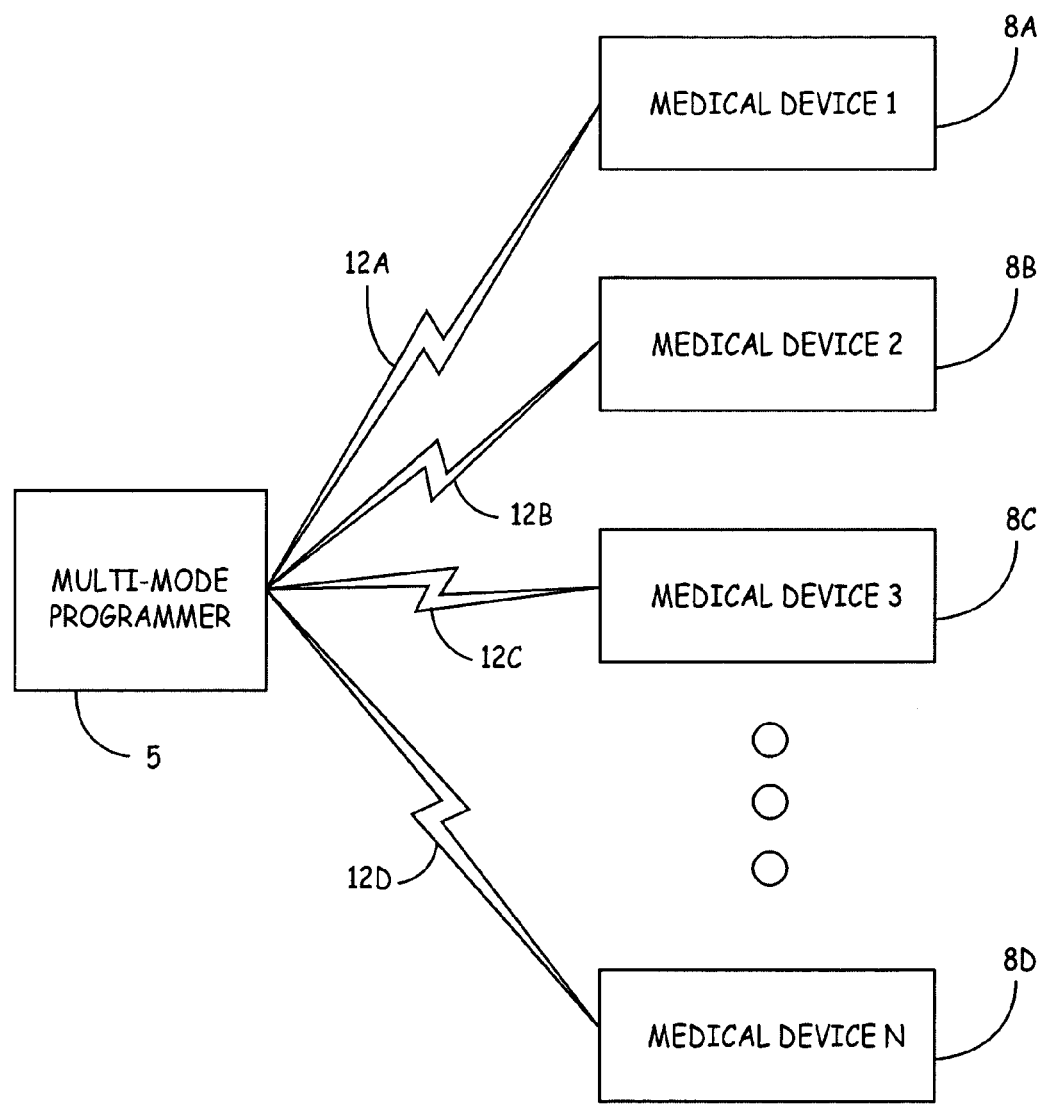
FIG. 2 is a block diagram illustrating telemetry between a multi-mode programmer and a set of different medical devices.

FIG. 2 is a block diagram illustrating telemetry between programmer 5 and a set of different medical devices 8A–8D. Again, the different medical devices 8A–8D may comprise any of a wide variety of medical devices, including implanted and non-implanted medical devices, used to deliver therapy to humans, mammals, or even other types of living beings. In accordance with the invention, the different devices 8A–8D communicate using different telemetry techniques. In other words, the format of telemetry signal 12A is different from that of 12B, 12C and 12D. For example, different telemetry signals 12 may have distinct carrier waveforms defined by amplitude and frequency. Also, different telemetry signals 12 may be modulated differently, e.g., using amplitude modulation (AM), frequency modulation (FM), pulse width modulation (PWM), pulse code modulation (PCM), pulse position modulation (PPM), or the like. Also, different coding schemes may be associated with different signals 12, such as phase-shift keying (PSK), orthogonal coding, frame based coding, or the like. Programmer 5 may identify these unique characteristics of the raw signal without performing a demodulation in order to identify the communication mode. An appropriate demodulator can then be selected, as well as appropriate signal transmission techniques and components.

Programmer 5 supports communication with the different devices 8A–8D by supporting communication via each of the different telemetry communication modes associated with signals 12A–12D. In particular, programmer 5 selectively switches communication modes to match the communication mode of medical device 8, and thereby permit programming, interrogation or both. Programmer 5 may be configured to receive signals in a frequency band known to correlate to all of telemetry signals 12, or may periodically tune to different frequency bands to tune for reception of different telemetry signals 12 over time.

The different medical devices 8A–8D may correspond to different types of devices, i.e., devices that deliver different types of therapy. Alternatively medical devices 8A–8D may comprise similar devices manufactured by different companies, which use different telemetry techniques. In addition, medical devices 8A–8D may correspond to similar devices manufactured by the same company, but which use different telemetry techniques.

In most cases, medical devices 8A–8D correspond to different devices implanted or used on different patients. In some cases, however, medical devices 8A–8D may correspond to different devices implanted or used in one particular patient. In other words, a patient may have more than one medical device 8 implanted within his or her body. In that case, programmer 5 may support communication with all of the different devices implanted and used within the same patient. In any case, the need for distinct programmers for each device can be eliminated in favor of a single multi-mode programmer 5 that supports a plurality of communication modes.

Figure 3:
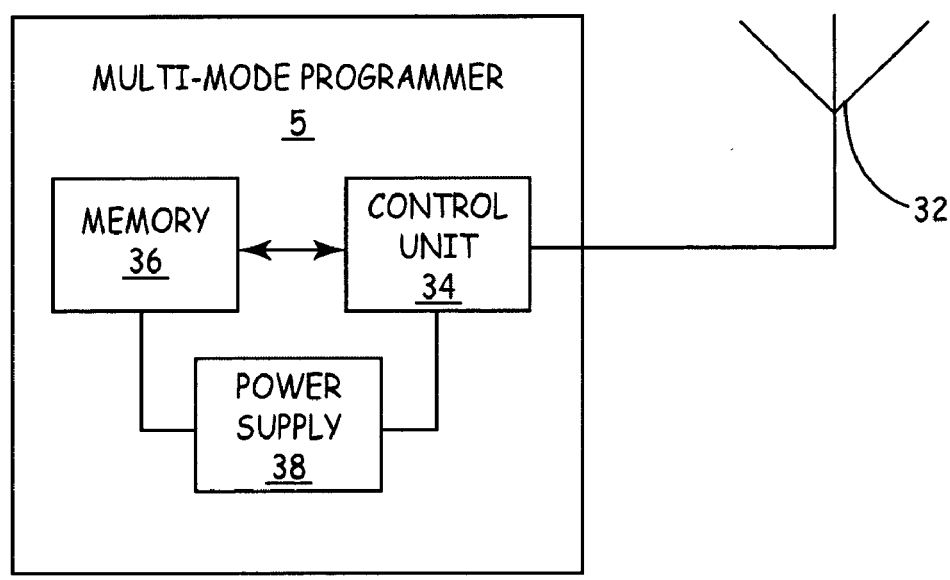
FIG. 3 is a block diagram of a multi-mode programmer that supports a plurality of communication modes for communicating with different medical devices via different telemetry techniques.

FIG. 3 is an exemplary block diagram of a programmer 5 that supports a plurality of communication modes for communicating to different medical devices via different telemetry techniques. Programmer 5 is configured to dynamically select different communication modes according to the communication modes presented from medical devices 8. As illustrated, programmer 5 may include an antenna 32, a control unit 34, a memory 36, and a power supply 38.

Antenna 32 may send and receive different electromagnetic telemetry signals 12, such as radio frequency signals, as directed by control unit 34. The invention, however, is not limited for use with electromagnetic telemetry signals, but may also used with other telemetry signals, including sound waves. In addition, in some embodiments, programmer 5 may use the patient's flesh as a transmission line for communication of electromagnetic signals between medical devices and programmer 5.

In any case, programmer 5 supports communication according to a plurality of telemetry modes. In operation, control unit 34 of programmer 5 receives telemetry signals via antenna 32. Antenna 32 may be tuned to a large frequency band that covers any possible telemetry signal that may be received from a device supported by programmer 5, or may be periodically tuned by control unit 34 to individual frequencies that correspond to specific telemetry signals that are supported. In any case, once a signal is received, control unit 34 conditions received signals so that signatures associated with the received signals can be identified. For example, control unit 34 may perform amplification or attenuation on received signals, and may also implement a phase locked loop to properly synchronize the phase of a received signal with the signatures to which the received signal is being compared.

The signatures may correspond to templates of expected waveforms that correspond to possible telemetry signals that could be received. The signatures may include distinctive waveform characteristics indicative of the respective telemetry signal, such as a particular frequency, amplitude, shape, modulation characteristic, or the like. Memory 36 stores the signatures for every telemetry technique that is supported by programmer 5. Accordingly, control unit 34 compares received signals with stored signatures by accessing memory 36. Then, after identifying an acceptable match between a stored signature and a received telemetry signal, e.g., 12A, programmer 5 is able to identify the telemetry technique associated with the medical device that sent signal 12A. In other words, the received signals can be compared to signatures, and the signatures can be mapped to communication modes.

Memory 36 may also store configuration parameters associated with different communication modes for control unit 34. In addition, memory 36 may include a lookup table (LUT) that maps signatures to communication modes, i.e., by mapping a number associated with a signature to a number associated with an associated communication mode. Thus, upon identifying a signature associated with a received telemetry signal 12A, control unit can access the LUT in memory 36 to select the proper communication mode. Then, control unit 34 can be configured according to the selected communication mode to output telemetry signals that the medical device associated with the received telemetry signal 12A can understand. In addition, control unit 34 can configure itself so that signals sent from the respective device can be properly demodulated and interpreted. In short, the different communication modes supported by programmer 5 can be programmed into memory 36, and then applied on a selective basis based on received telemetry signals 12.

Figure 4:
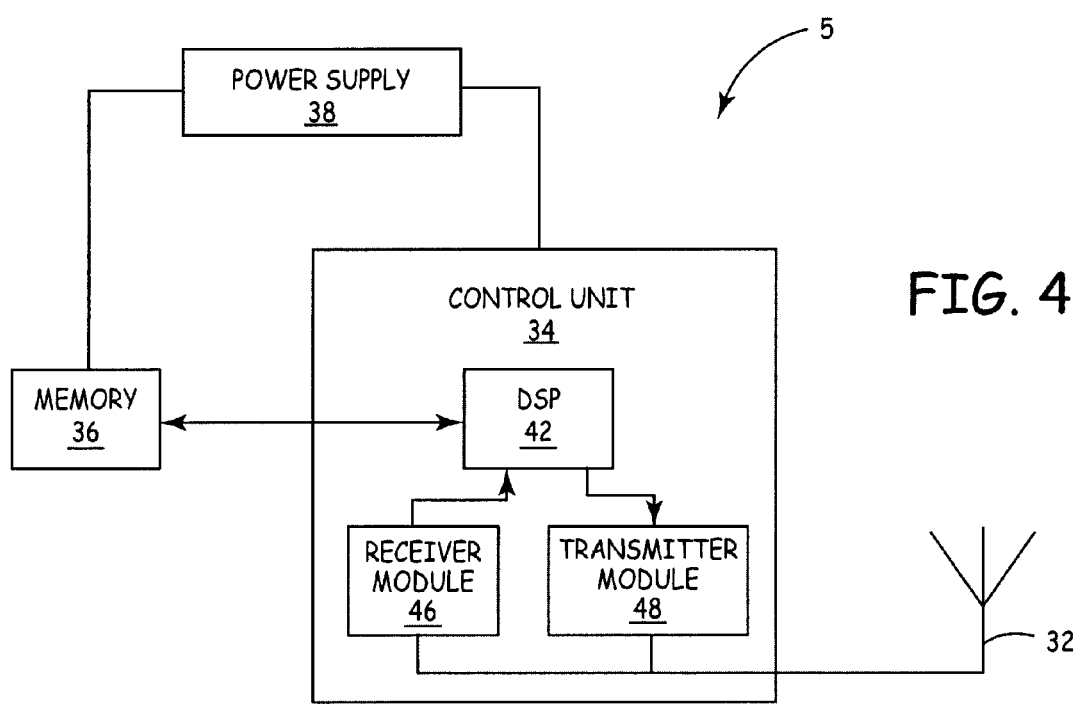
FIG. 4 is a more detailed block diagram of a multi-mode programmer according to an embodiment of the invention.

FIG. 4 is a more detailed exemplary block diagram of programmer 5. As illustrated, programmer 5 includes a power supply 38, such as a battery, that powers control unit 34 and memory 36. Antenna 32 is coupled to control unit 34 to facilitate the reception and transmission of wireless electromagnetic telemetry signals. The invention, however, is not necessarily limited for use with wireless signals or electromagnetic signals. Again, similar principles can be applied in a programmer that can be wired to one or more medical devices, or a programmer that uses the patient's flesh or sound waves as the transmission medium for telemetric communication.

Control unit 34 may include a programmable digital signal processor (DSP) 42 coupled to a crystal oscillator (not shown). Examples of suitable DSPs include the TI-TMS320C2000 family of DSPs, such as the model number TI-TMS320LC2406 DSP, commercially available from Texas Instruments Incorporated of Dallas Tex., USA. By way of example, the oscillator may comprise a 5 MHz crystal, although other oscillators could be used. The TI-TMS320LC2406 DSP is a 16-bit fixed point DSP originally designed for motor control applications. The TI-TMS320LC2406 DSP includes internal flash memory and a 10-bit analog to digital converter (ADC). Other DSPs and programmable microprocessors, however, could alternatively be used.

Memory 36 may comprise a removable memory card that couples to DSP 42 via a memory connector, although non-removable memory could also be used. Removable memory cards can provide an added benefit in that the card can be removed from programmer 5 and sent to a physician for analysis. For example, after programmer 5 telemetrically communicates with a given medical device 8, data from that medical device may be stored in memory 36. The data stored in memory 36 may be data selected by programmer 5. In some cases, the data stored in memory 36 may be overflow data from an internal memory associated with medical device 8, allowing programmer 5 to provide more continuous and more prolonged patient monitoring capabilities. If memory 36 comprises a removable card, the card may be removed from programmer 5 and sent to a physician, and a new card may be inserted in its place. In this manner, data from a medical device 8 can be easily provided to a physician, e.g., to facilitate early diagnosis of problems.

Moreover, the use of memory cards can avoid the need to send the whole programmer 5 to the physician. In addition, a more continuous and larger sample of data from the medial device may be captured by sequentially inserting a number of memory cards into programmer 5 over a period of time in which information is being sent from the respective medical device. As one example, memory 36 may comprise a 64 or 256 Megabyte multimedia memory module commercially available by SanDisk of Sunnyvale, Calif., USA. Other removable or non-removable memory, however, may also be used.

Another advances in the art of removable memory cards and a DSP relates to updating the function of the programmer 5. For example, in order to update programmer 5 to support new or different forms of telemetric communication, a different memory card, storing software to support the new or different telemetry may be provided. In other words, a DSP configuration with removable memory provides advances in the art in terms of scalability of programmer 5. If new or different telemetry is developed, software can be likewise devolved and provided to programmer via a new removable memory card. Accordingly, in that case, the need to develop a different programmer may be avoided. Instead, new algorithms can be provided to programmer 5 via a new memory card that stores new instructions that can be executed by the DSP.

Antenna 32 may comprise any of a wide variety of antenna configurations. In one particular example, antenna 32 may comprise a substantially flat, co-planer dual opposing coil antenna. For example, two opposing coils may be formed on a common substrate to provide two signal inputs to control unit 34. The input of two or more signals to control unit 34 may simplify signal processing within control unit 34, such as by simplifying filtering. In addition, an antenna scheme utilizing multiple concentric and co-planar antenna coils on a substrate may also reduce the form factor of programmer 5, which can facilitate wearable embodiments. The use of concentric and co-planar antenna coils may also improve the reception of telemetry signals in a noisy environment.

Power supply 38 may comprise any of a wide variety of batteries or other power sources. For example, power supply 38 may comprise a rechargeable or non-rechargeable battery, such as a polymer or foil battery, a lithium ion batter, a nickel cadmium battery, or the like. The battery may have a voltage range of approximately 4.2 to 3.0 volts throughout its useful service life and a capacity of 1.5 Ah, although the invention is not limited in that respect.

In addition to DSP 42, control unit 34 of programmer 5 may include a receiver module 46 and a transmitter module 48. Receiver module 46 and transmitter module 48 may be integrated or may comprise separate circuits. The composition of receiver module 46 and transmitter module 48 may depend on the particular DSP 42 used in control unit 34 as well as the particular communication modes supported by programmer 5.

In general, receiver module 46 conditions a received telemetry signal for analysis by DSP 42. Receiver module 46 may include an analog-to-digital converter (ADC), although some DSPs, such as the TI-TMS320LC2406 mentioned above, include an ADC as part of the DSP. Receiver module 46 may also include one or more amplifiers, a variable gain amplifier (VGA), one or more filters, automatic gain control (AGC), if needed, and a phase-locked loop for synchronizing a received signal so that an in-phase sample can be identified. These and/or other components of receiver module 46 condition a received telemetry signal as required by DSP 42 so that signal analysis can be performed. In some cases, DSP 42 may configure both itself and receiver module 46 for reception of a given telemetry signal that is expected, such as by selectively switching on a subset of the bandpass filters in DSP 42 and controlling the gain of a received signal in receiver module 46.

Transmitter module 48 conditions output signals for wireless transmission to a medical device via antenna 38. For example, DSP 42 may generate timed output signals based on a selected communication mode in order to communicate with the respective medical device 8 via telemetry. Transmitter module 48 can receive signals from DSP 42 and amplify the signals for transmission via antenna 38. For example, transmitter module 48 may include transmit circuitry for driving antenna 38, such as a set of field effect transistors (FET) that output relatively large output voltage pulses in response to relatively small input voltages received from DSP 42. Transmitter module 48 may also include various other filters, amplifiers, or the like, that may be selectively activated based on the given communication mode. For example, in some cases, a selected communication mode identified by DSP 42 can cause DSP 42 to send control signals to transmitter module 48 to configure transmitter module 48 for telemetric communication consistent with the selected communication mode. In any case, transmitter module 48 conditions output signals from DSP 42 for wireless telemetric transmission to a medical device.

DSP 42 of programmer 5 may include several different bandpass filters and several different demodulators, such as one or more amplitude demodulators, one or more frequency-shift keyed (FSK) demodulators, one or more phase-shift keyed (PSK) demodulators, and the like. For example, these different components may be programmed as software or firmware. In any case, DSP 42 selects the particular bandpass filter(s) and demodulator type to process the digitized signal according to the communication mode that is selected. In other words, DSP compares the raw signal that is received to signatures in order to identify the appropriate communication mode, and then selectively enables the appropriate demodulator so that subsequent signals can be demodulated and interpreted.

An additional function implemented by DSP 42 may include the control of a variable-gain amplifier (VGA) or other components included in receiver module 46 or transmitter module 48. For example, this may further ensure that the receiver module 46 supplies to the A/D converter of DSP 42 a signal having a desired peak amplitude. Moreover, VGA control in the DSP 42 may provide flexibility in software so that adjustments can be made to properly condition a wide variety of telemetry signals.

In order to facilitate the automatic gain control (AGC) between DSP 42 and receiver module 46, receiver module 46 may include a digital-to-analog (D/A) converter to convert a digital control word supplied from DSP 42 to a corresponding analog voltage level for variable-gain amplification.

One specific configuration of programmer 5 may be formed of the exemplary components listed above including the TI-TMS320LC2406 DSP, SanDisk memory module, a dual coil planer antenna, a sufficiently small battery, and individual hardware components to implement the receiver module 46 and transmitter module 48. In that case, programmer 5 may realize a compact form factor suitable for inconspicuous use by a patient, e.g., to collect information from a medical device and send the memory cards to the physician. A minimal amount of communication from programmer 5 to the medical device may prompt the medical device to uplink the requested information. For example, such exemplary components may be used to realize a programmer 5 having dimensions less than approximately 60 millimeters by 90 millimeters by 15 millimeters. In other words, programmer 5 can be made to dimensions corresponding roughly to the size of a thick credit card. Such reduced size can be particularly useful for wearable embodiments of programmer 5.

If desired, programmer 5 may also include an activation switch (not shown), to allow a patient to initiate communication with a medical device. For example, if the patient identifies pain or other problems, it may be desirable to initiate communication, e.g., to cause the medical device to communicate sensed information to programmer 5. In that case, an activation switch can provide the patient with the ability to ensure that sensed conditions are stored in programmer 5 during periods of time when physical problems may be occurring to the patient.

Moreover, programmer 5 may include other user interface features, such as a display screen, a speaker, or a blinking light. For example, feedback in the form of sound or light flashes, images, instructions, or the like may be useful to a patient, e.g., to indicate that communication has been initiated or to indicate to the patient that the programmer is positioned correctly for such communication.

Figure 5:
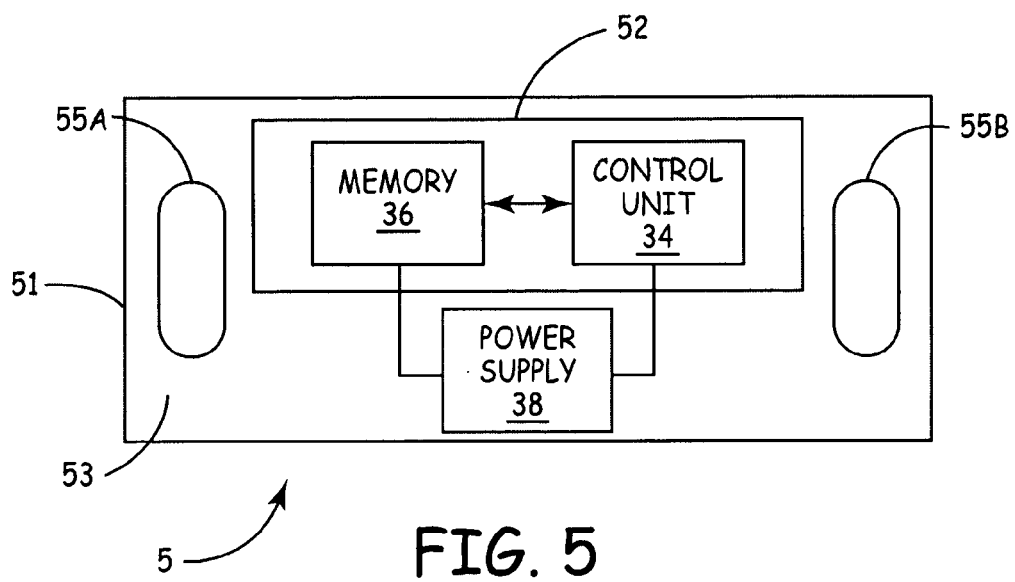
FIGS. 5 and 6 are diagrams illustrating an embodiment of a multi-mode programmer taking the form of an adhesive patch.
Figure 6:
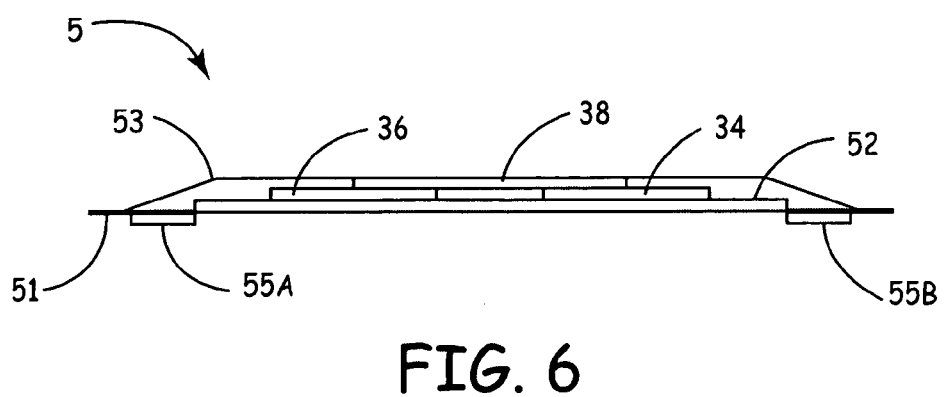

FIGS. 5 and 6 are diagrams illustrating one embodiment of programmer 5 in the form of an adhesive patch. In that case, programmer 5 may include an adhesive strip 51 for attaching programmer 5 to a patients skin. In addition, electrodes 55 may also be used to facilitate the reception of signals though the patients flesh, although the use of electrodes would not be necessary for every embodiment. In other words electrodes 55 may provide an alternative to antenna 52 for the transmission and reception of signals. Accordingly, both electrodes 55 and antenna 52 may be electrically coupled to control unit 34.

Programmer 5 (in this case a patch) is configured to dynamically select different communication modes according to the communication modes presented from medical devices 8. As illustrated, programmer 5 may include an antenna 52, a control unit 34, a memory 36, and a power supply 38, an adhesive strip 51, a protective sheath 53 and electrodes 55.

Antenna 52 may comprise a coplanar dual coil antenna that sends and receives electromagnetic telemetry signals as directed by control unit 34. Alternatively or additionally, electrodes 55 may be used to send and receive the signals. The protective sheath 53 may substantially encapsulate one or more of the components of programmer 5.

As outlined above, programmer 5 (in this case a patch) supports communication according to a plurality of telemetry modes. Control unit 34 compares received signals with stored signatures by accessing memory 36. Then, after identifying an acceptable match between a stored signature and a received telemetry signal, programmer 5 is able to identify the telemetry technique associated with the medical device that sent the signal.

Memory 36 stores the signatures and may also store configuration parameters associated with different communication modes for control unit 34. In addition, memory 36 may include a lookup table (LUT) that maps signatures to communication modes, i.e., by mapping a number associated with a signature to a number associated with an associated communication mode. Thus, upon identifying a signature associated with a received telemetry signal, control unit 34 can access the LUT in memory 36 to select the proper communication mode. Then, control unit 34 can be configured according to the selected communication mode to output telemetry signals that the medical device associated with the received telemetry signal can understand. In addition, control unit 34 can configure itself so that signals sent from the respective device can be properly demodulated and interpreted.

As mentioned above, memory 36 may comprise a removable memory card. Accordingly, memory 36 may be removed from programmer 5, such as via a slot or hole formed in sheath 53. Alternatively, sheath 53 may be pulled back to expose memory 36, allowing memory 36 to be removed or replaced and possibly sent to a physician for analysis.

In still other embodiments, programmer 5 may be embodied in a wrist watch, a belt, a necklace, a pendent, a piece of jewelry, an adhesive patch, a pager, a key fob, an identification (ID) card, a laptop computer, a hand-held computer, or other mechanical configurations. A programmer 5 having dimensions less than approximately 60 millimeters by 90 millimeters by 15 millimeters can be particularly useful for wearable embodiments. In particular, a configuration similar that that illustrated in FIGS. 5 and 6 using the exemplary components listed herein may be used to realize a programmer with a small enough form factor to facilitate different wearable embodiments. Additional components may also be added, such as a magnet or electromagnet used to initiate telemetry for some devices.

Figure 7:
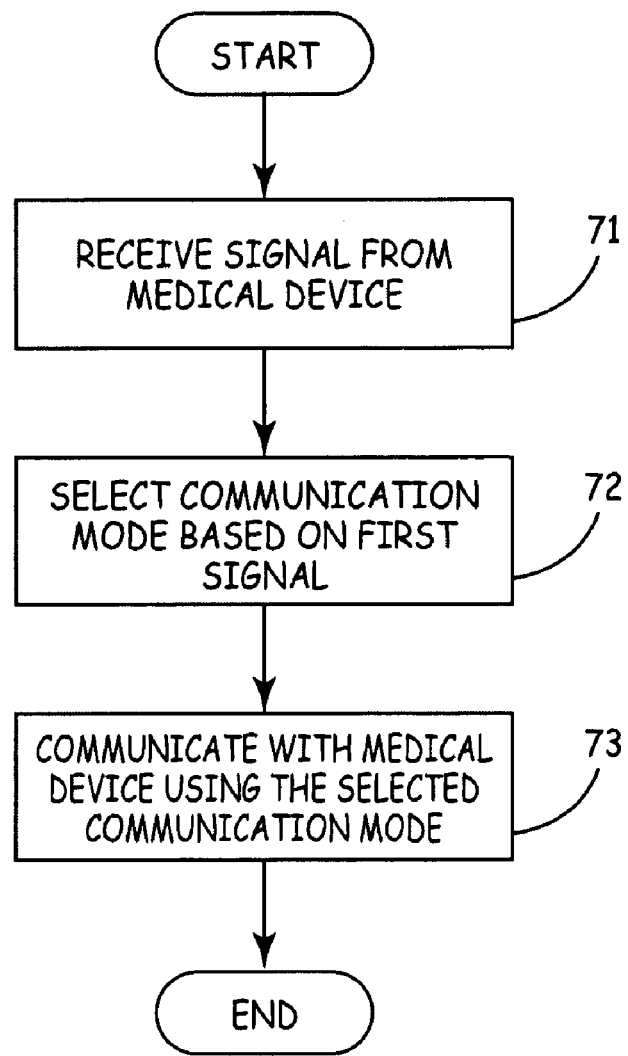
FIGS. 7 and 8 are flow diagrams illustrating techniques in accordance with embodiments of the invention.

FIG. 7 is a flow diagram illustrating a technique consistent with the principles of the invention. As shown, programmer 5 receives a telemetry signal 12 from a medical device 8 (71). Control unit 24 of programmer 5 selects a communication mode based on the received signal (72). Programmer 5 then communicates with medial device 8 using the selected communication mode (73).

In order to select the proper communication mode based on the received signal (72), control unit 24 of programmer 5 may identify a signature associated with the received signal. More specifically, receiver module 46 conditions a received telemetry signal so that it falls within the dynamic range of DSP 42. DSP 42 samples the conditioned signal and compares the digital sample to various signatures stored in memory 36. For example, DSP 42 may perform a correlation operation to compare a digital sample of a received signal to various signatures stored in memory 36. In particular, the correlation operation may compare the frequencies, phase shifts, pulse widths, or any other variable between the digital sample of the received signal to those of the different signatures. Upon identifying a signature that matches the digital sample of the received signal to within an acceptable degree (which may also be programmable), DSP 42 can configure programmer 5 according to a communication mode associated with the signature. In other words, once the appropriate signature has been identified, DSP 42 can select a communication mode, such as by accessing a LUT in memory 36 that maps signatures to communication modes.

Upon identifying the necessary communication mode for telemetric communication with a respective medical device 8, control unit 34 configures for such communication. For example, DSP 42 may select an appropriate set of bandpass filters and an appropriate demodulator, each of which may be software implemented as part of DSP 42. In addition, in some cases, DSP 42 may send control signals to receiver module 46 and transmitter module 48 to configure those modules 46, 48 for respective reception and transmission consistent with the selected communication mode. In this manner, programmer 5 can be configured for communication according to a first telemetric mode of communication, and then reconfigured for communication according to a second (different) telemetric mode of communication. In some cases, a large number of different communication modes can be supported by programmer 5.

Figure 8:
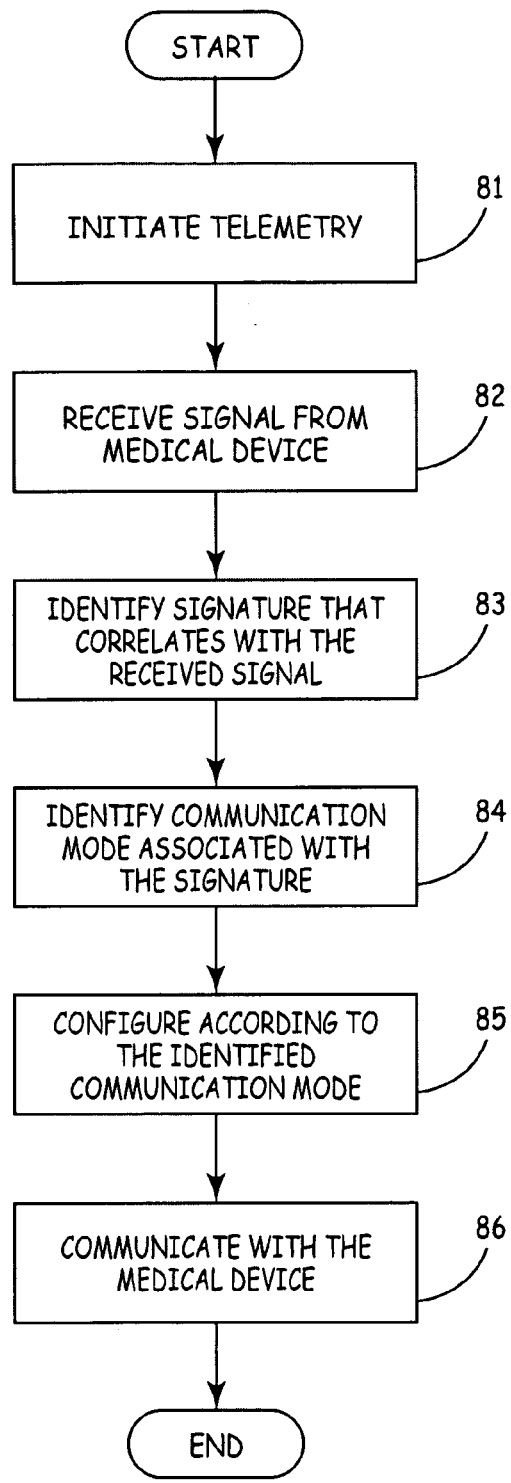

FIG. 8 is another flow diagram illustrating a technique consistent with the principles of the invention. As shown, programmer 5 initiates telemetry with a medical device 8 (81). In most cases, in order to preserve battery life in a medical device, the medical device does not send telemetry signals unless it receives a request for such signals. Accordingly, programmer 5 can be configured to initiate telemetry with medical devices (81) by sending an appropriate request. Moreover, since the initiation required to cause a given medical device to send a telemetry signal may differ with the device, programmer may perform a plurality of initiation techniques so as to cause any device supported by programmer 5 to send a telemetry signal.

For some devices, a magnetic field may be used to initiate telemetry, such as by magnetically activating a switch on the respective device to cause the device to send telemetry signals. Accordingly, programmer 5 may include a magnet or an electromagnet that generates the required magnetic field to cause the medical device to send a telemetry signal. For other devices, telemetry from a medical device 8 may begin upon receiving a particular wireless signal that corresponds to a request for telemetry. Accordingly, control unit 24 of programmer 5 may be configured to send one or more different request signals to provoke a response from the medical device. In some cases, control unit 24 may send different request signals over time to provoke responses from different medical devices for which programmer 5 supports telemetry. Thus, if a particular device is in proximity to programmer 5, eventually the appropriate request signal will be sent from programmer 5 to that device.

In any case, once programmer 5 has initiated telemetry with the medical device (81) causing the medical device to send a telemetry signal, programmer 5 receives the signal from the medical device (82). Control unit 24 of programmer 5 identifies a signature stored in memory 26 that correlates with the received signal (83). More specifically, DSP 42 generates a digital sample based on a signal conditioned by receiver module 46, and compares the digital sample to the signatures stored in memory by invoking a correlation operation.

Upon identifying a signature stored in memory 26 that correlates with the received signal (83), control unit 24 identifies a medical device associated with the signature (84). More specifically, DSP 42 accesses a LUT in memory 26, which maps signatures to communication modes, and selects from the LUT, the communication mode associated with the identified signature.

Control unit 24 then configures programmer 5 for communication with the medical device 5 according to the selected communication mode (85). More specifically, DSP 42 selects particular bandpass filter(s) and a demodulator to process received telemetry signals in accordance with the communication mode that is selected. In addition, DSP 42 may send control signals to one or more components included in receiver module 46 or transmitter module 48 to configure the modules to condition received signals and to condition output signals according to the communication mode that is selected.

Programmer 5 can then telemetrically communicate with the medical device (86). This telemetric communication may be used for any of a wide variety of desirable communication that can occur between a programmer and a medical device. For example, programmer 5 may telemetrically communicate with the medical device to program a new therapy technique into the medical device. In particular, device 5 may be configured to receive input from a physician or medical personnel specifying a therapy to be performed, and may send a signal to the medical device according to the selected communication mode to direct the medical device to perform the therapy.

Alternatively, programmer 5 may telemetrically communicate with the medical device 8 to request stored information corresponding, for example, to diagnostic information, sensed conditions associated with the patient, information relating to therapy delivered to the patient, or any other information collected or identified by the medical device. In that case, programmer 5 may receive the requested information from the medical device in response to the request for stored information sent according to the appropriately selected communication mode. These or other communications may occur between a medical device and programmer 8 once programmer has identified the appropriate communication mode, and configured according to that communication mode consistent with the principles of the invention.

Figure 9:
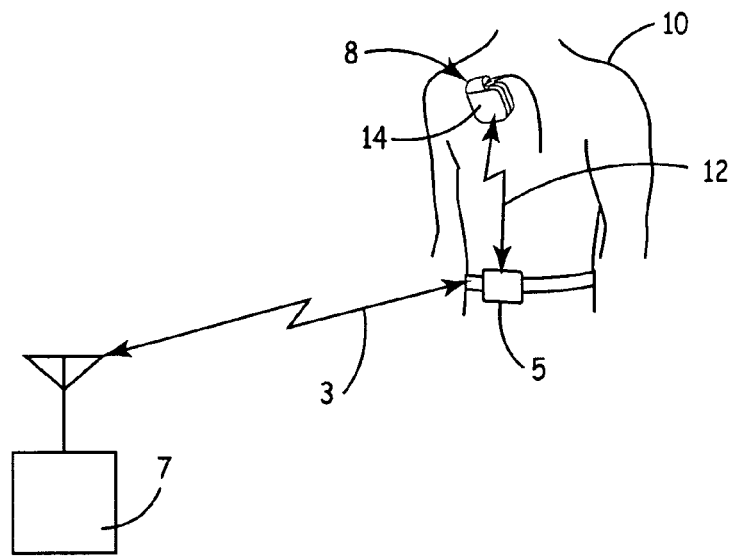
FIG. 9 is a diagram illustrating an alternative embodiment utilizing the multi-mode programmer of the invention.

FIG. 9 is a conceptual diagram illustrating an alternative embodiment utilizing the multi-mode programmer 5 of the present invention communicating with an exemplary medical device 8 implanted in a human body 10 and, additionally, communicating to an external remote monitor 7 that may be connected to a network (in a hospital or clinic) or to the Internet for long distance remote monitoring. This embodiment illustrates a system that allows the retrofitting of the existing implant base of near field telemetry pacemakers and defibrillators (totaling several million devices implanted worldwide) to be simply, inexpensively and with no patient trauma updated to a far field telemetry system to allow the remote monitoring of this group of patients. Implantable medical device 8 represents one of a variety of medical devices that may communicate with programmer 5. Although illustrated as an implantable cardiac pacemaker, medical device 8 may take the form of a variety of other medical devices such as, for example, an implantable defibrillator, an implantable pacemaker/cardioverter/defibrillator, an implantable muscular stimulus device, an implantable brain stimulator, an implantable nerve stimulator, an implantable drug delivery device, implantable monitor, or the like. Multi-mode programmer 5 may take the form of a belt worn pager like device, a pendant worn around the patient's neck, a wrist worn watch like device, a tape-on patch-like device or any other form factor that allows improved patient comfort and safety for long term monitoring.

In the example shown in FIG. 9, medical device 8 includes a hermetically sealed enclosure 14 that may include various elements, although the invention is not limited to hermetically sealed devices. By way of example, enclosure 14 may house an electrochemical cell, e.g., a lithium battery, circuitry that controls device operations and records sensed events, physiological activity and patient conditions, and a control unit coupled to an antenna to transmit and receive information via wireless telemetry signals 12.

Programmer 5 communicates with medical device 8 via near field telemetry signals 12—an exemplary telemetry system is as substantially described in U.S. Pat. No. 4,556,063 to Thompson, et al. and U.S. Pat. No. 5,127,404 to Wyborny, et al. and incorporated herein, in relevant parts, by reference in their entireties. Numerous near field telemetry systems may alternatively be used for example telemetry systems such as described in U.S. Pat. No. 4,223,679 to Schulman, et al, U.S. Pat. No. 4,532,932 to Batty, et al, U.S. Pat. No. 4,562,840 to Batina, et al, U.S. Pat. No. 4,681,111 to Silvian, U.S. Pat. No. 4,847,617 to Silvian, U.S. Pat. No. 5,137,022 to Henry and U.S. Pat. No. 5,342,408 to deCoriolis.

Programmer 5 may use telemetry signals 12 to program medical device 8 to deliver a particular therapy to human body 10, such as electrical stimulation, drug administration or the like. In addition, medical device 8 may use telemetry signals 12 to send information to programmer 5 such as diagnostic information, sensed conditions associated with the patient, information relating to therapy delivered to the patient, or any other information collected or identified by medical device 8. In this manner, telemetry allows communication between medical device 8 and programmer 5. Additionally programmer 5 communicates to the remote monitor device 7 via far field telemetry signals 3—as substantially described in U.S. Pat. No. 5,683,432 to Goedeke, et al and incorporated herein by reference in its entirety. For example, the system described in association with FIG. 9 may allow remote monitoring of high-risk CHF or arrhythmia patients as substantially described in U.S. Pat. No. 5,752,976 "World Wide Patient Location and Data Telemetry System for Implantable Medical devices" to Duffin et. al. and incorporated herein by reference in its entirety.

Alternatively, telemetry signal 3 may consist of an infrared communication link such as IrDA or, a second alternative, ultrasound communication link to remote monitor device 7.

Figure 10:
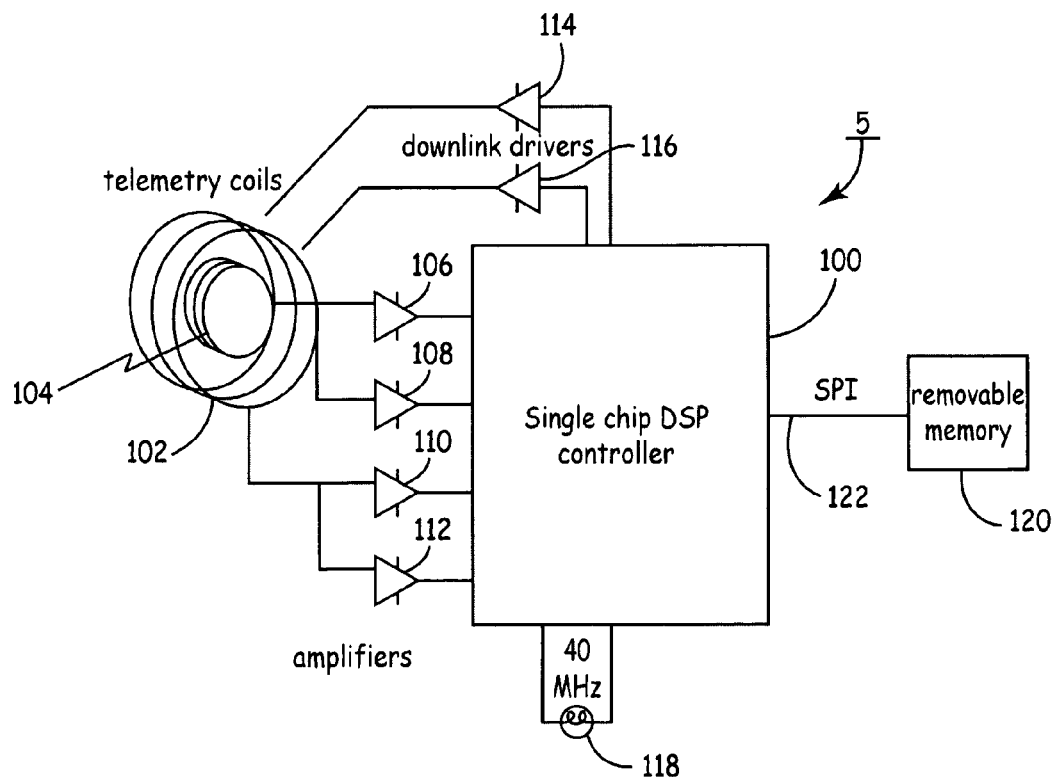
FIG. 10 is a simplified schematic representation of the software based multi-mode programmer of the present invention.

FIG. 10 is a simplified schematic representation of a DSP/software based multi-mode transmitter/receiver/programmer of the present invention. Programmer 5 consists of a single chip digital signal processor (DSP) 100 and a minimal amount of additional support circuitry. Examples of suitable DSPs include the TI-TMS320C2000 family of DSPs, such as the model number TI-TMS320LC2406 DSP, commercially available from Texas Instruments Incorporated of Dallas Tex., USA. The TI-TMS320LC2406 DSP is a 16-bit fixed point DSP, low cost, fully static with low power modes originally designed for motor control applications. The TI-TMS320LC2406 DSP includes internal flash memory and a 16 channel 10-bit analog to digital converter (ADC) with 2 Ms/s capability. Other DSPs and programmable microprocessors, however, could alternatively be used.

In addition to the DSP 100, FIG. 10 shows a minimal amount of support circuitry including the unique antenna scheme within the programmer head as substantially described in U.S. Pat. No. 6,298,271 "Medical System Having Improved Telemetry" to Weijand incorporated herein by reference in its entirety. The antenna scheme utilizes a first antenna 102 and a second antenna 104, the antennas disposed in a concentric and co-planar manner. The smaller area antenna 104 (in this exemplary case the area of antenna 104 is ¼ the size of antenna 102) contains 4 times the number of turns of the larger antenna 102. This concentric and co-planar disposition permits the cancellation of far field signals (i.e., noise) and the reception of near field differential signals. It also permits the multi-mode programmer or peripheral memory patch to be much smaller and, thus, a more portable size than was previously possible. Additionally, the antenna design results in a significant reduction in circuit design complexity. Low noise, wide band amplifiers 106, 108, 110 and 112 amplify the received antenna signals and input them to the DSP 100 ADC inputs for sampling. Downlink drivers 114 and 116 under control of DSP 100 provide downlink telemetry to an implanted medical device 8. Optionally, the SPI bus interface 122 and removable memory 120 may be added for a peripheral memory embodiment. The oscillator 118 may comprise a 40 MHz crystal, although other oscillators could be used.

Figure 11:
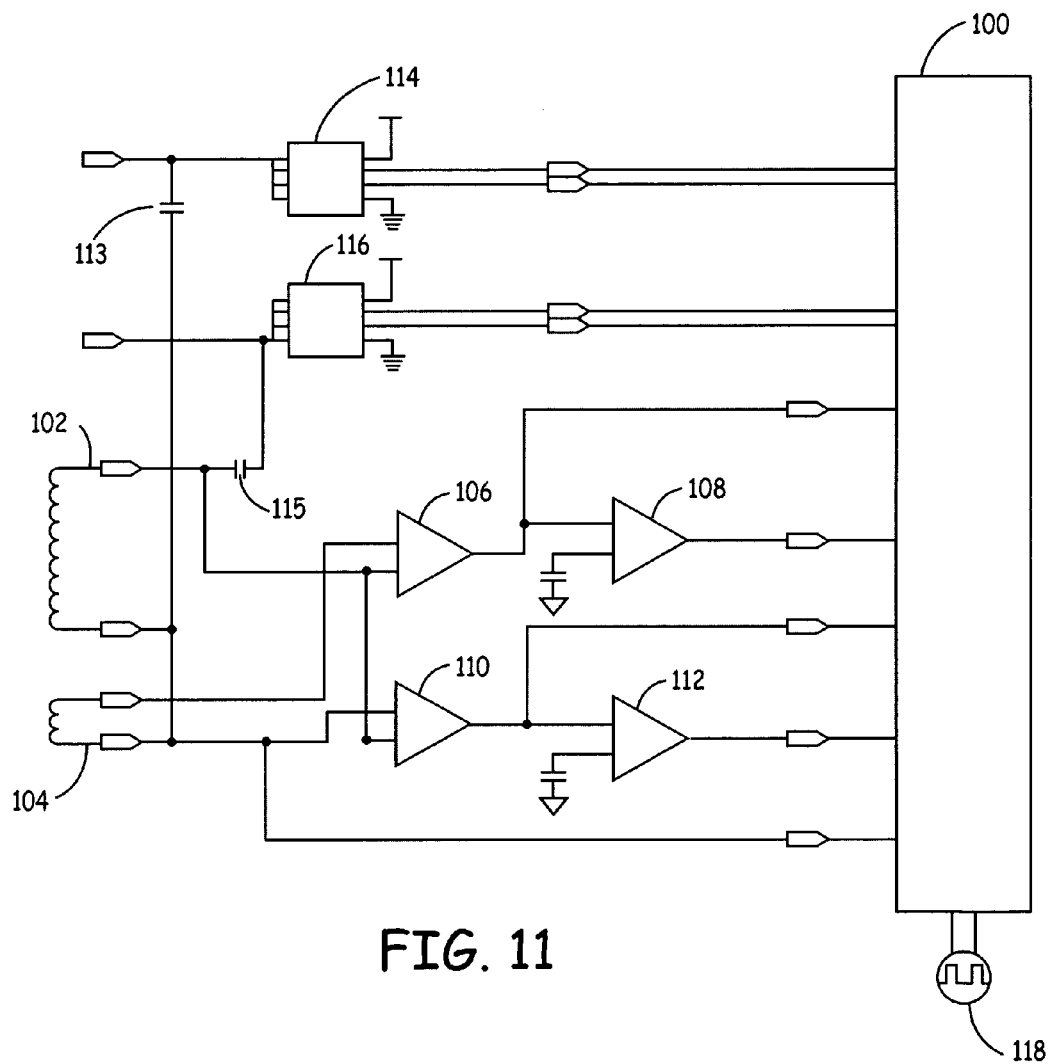
FIG. 11 is a schematic diagram of the front-end receiver, transmitter coil interface and DSP portions of the multi-mode programmer according to an embodiment of the invention.

FIG. 11 is a schematic diagram of the front-end receiver, transmitter coil interface and DSP portions of the multi-mode programmer 5 according to one embodiment of the invention. The antenna system consists of two coils—an outer, larger coil 102 and an inner, smaller coil 104. Inner coil 104 has a larger number of turns than outer coil 102 to match the inductance of the two coils. The difference signal from the two coils allows a near field telemetry signal to be received while rejecting far field noise signals as described in the above referenced '271 patent to Weijand. In an uplink mode of operation, fixed gain amplifiers 106, 108, 110 and 112 amplify the received telemetry signal and provide 4 analog signal channels to the DSP ADC inputs (described below). In a downlink mode of operation, capacitors 113 and 115 and driver switches 114 and 116 control the transmission to an implantable medical device 8. Independent control of the switches 114 and 116 by the DSP 100 allow non-overlap switch control to most efficiently drive the antennas while in a downlink mode of operation. The circuit of FIG. 11 is powered by a battery and may include an optional voltage regulator (both not shown).

The DSP 100 contains a 16-channel, 10 bit analog to digital converter (ADC) with independent ADC controller that samples and digitizes the 4 analog signals from amplifiers 106, 108, 110 and 112. The MAC processor under control of instructions contained in embedded memory in the DSP 100 processes, filters and demodulates the data samples received from the antenna system 102/104 from any of a large variety of conventional implantable devices. For ease of understanding, reference is made to the block diagram of FIG. 12, which depicts these functions in equivalent signal processing blocks.

Figure 12:
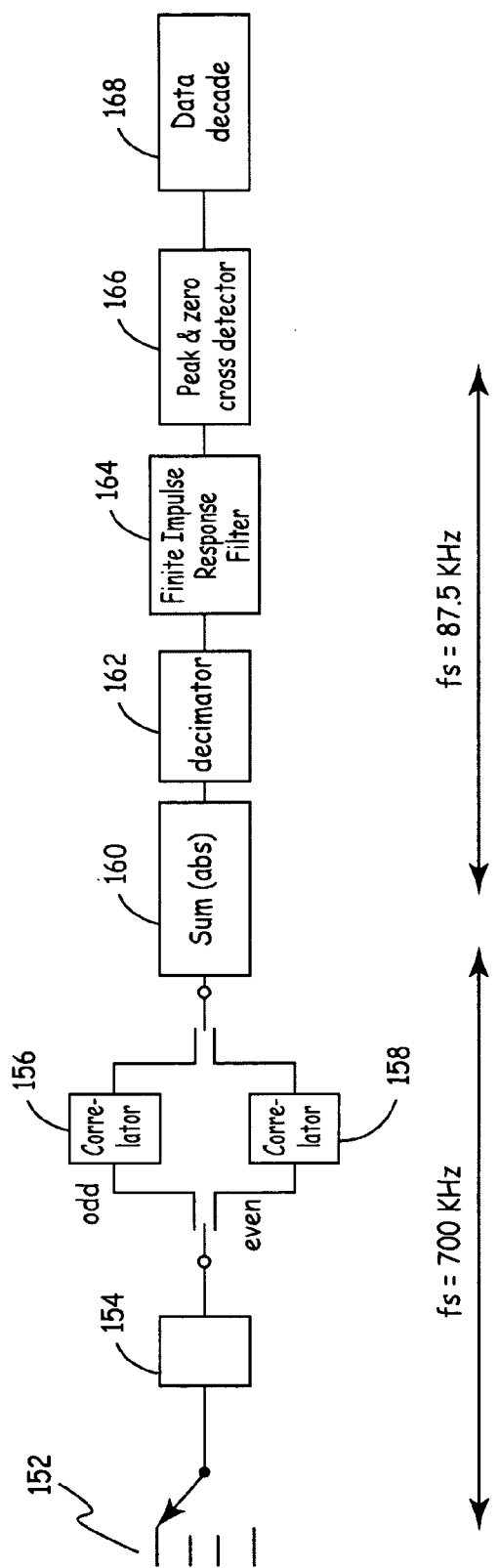
FIG. 12 is a diagram of the uplinked RF telemetry signal from an implanted medical device showing one embodiment of ping detection and demodulation.

FIG. 12 is a block diagram showing one embodiment of uplink telemetry ping detection and demodulation. The received and amplified signals are selected by multiplexer 152 and inputted to ADC 154 where they are converted at a rate of 700 kHz; the signal path is split into separate processing for odd and even samples. The odd 156 and even 158 correlators correlate the signal with an exponentially decaying sinusoid manner similar to the uplink pulse as described in the aforementioned '063 patent. As the correlator coefficients are zero every other sample (175 Khz signal sampled at 700 kHz) the odd and even correlators are just half the size of the full correlator. The results are absolute valued and summed 160 before being downsampled at 87.5 kHz (162) and filtered in FIR filter 164. Further processing detects peak and zero crossings 166 and frame and data decoding 168. Alternative telemetry systems may require different ADC conversion rates, signal conversion processes and demodulation techniques. For example, this invention may be used to detect, demodulate and decode any of the following signal types; amplitude modulation (AM), frequency modulation (FM), pulse width modulation (PWM), pulse code modulation (PCM), pulse position modulation (PPM), or the like. Also, different coding schemes may be associated with different signals 12, such as phase-shift keying (PSK), orthogonal coding, frame based coding, or the like.

Figure 13:
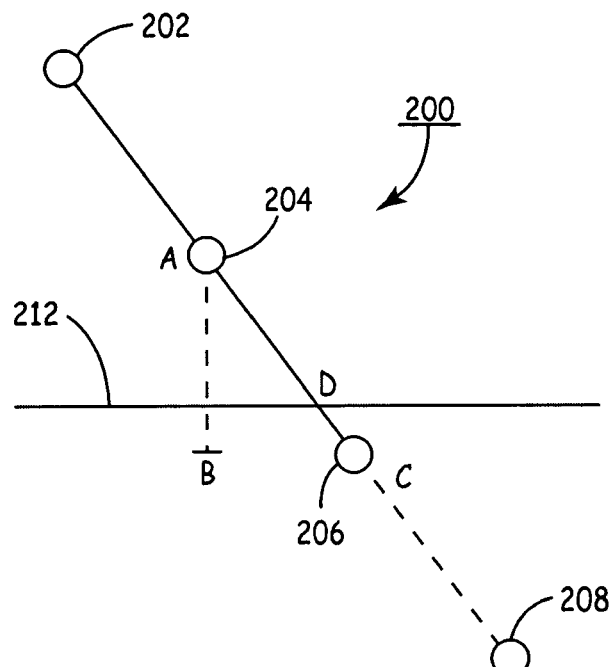
FIG. 13 is a diagram of an uplinked RF signal showing a zero crossing extrapolation according to an embodiment of the invention.

FIG. 13 is a diagram of an uplinked RF signal 200 showing a zero crossing extrapolation (FIG. 12 processing block 166) according to an embodiment of the invention. ADC samples are shown at 202, 204, 206 and 208. Ground potential or zero signal value is denoted at 212. The extrapolated time of the zero crossing may be determined by the value (AD/AC)*time in uSec from sample 204 to 206. This extrapolation method allows a reduced ADC sample rate and thus a reduced battery power drain.

Figure 14:
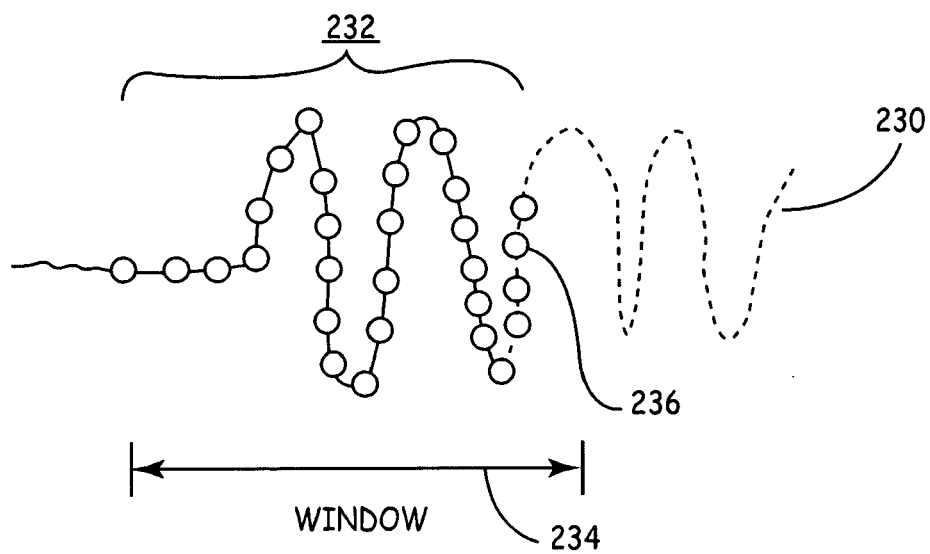
FIG. 14 illustrates an RF damped sinusoidal wave.

Additional power reduction concepts may be utilized individually or in tandem. Specifically, the TI DSP has reduced power states that may be enabled during circuit inactivity. Additionally, the timing of many IMD uplink telemetry systems are crystal controlled allowing the system of FIG. 11 to be powered down into a sleep mode and awakened during a window of expected or possible uplink signal transmission. FIG. 14 shows a RF damped sinusoid 230 from a typical pulse position modulation uplink system from an IMD. The DSP of FIG. 11 powers down after the previous pulse reception/detection and awakens, opening a window 234 of a discrete length at the next possible signal interval, enabling the ADC to begin sampling the signal 232 received by the antenna. After the detection of 2 cycles of the pinged signal (at 236), the ADC conversion is again disabled, conserving power. Lastly, the proper selection of the system clock allows the slowing down of the clock when low speed processing is required.

The interrupt structure of the exemplary system includes a slow interrupt service routine (ISR) for detection of frames and other service routines uses a 16 bit timer running at fc/4; this means it is started every 6.55 msec. At this rate the slow ISR can be several 1000's machine cycles long without affecting the DSP bandwidth.

The fast ADC ISR or other ISRs, as required, can interrupt the slow ISR routine. In the preferred embodiment, the fast ADC ISR running at 87.5 kHz has the highest priority. The fast ISR is activated when 16 ADC samples are converted.

A fast ISR is capable of detecting a telemetry ping and supplying a value for the signal strength. Upon detection the momentary value of the slow ISR timer is written (timestamp) and a value of the signal strength is written in two data buffers.

An automatic gain control routine uses the signal values of the detected pings and regulates the gain in the digital domain by applying a multiplication factor in the signal chain, or alternatively in the analog domain, by setting selecting a different gain stage input at the ADC input.

The gain is regulated towards a fixed target value such that the necessary division for the interpolation of the ping position (in the fast ISR) is reduced to a shift operation.

The values of the signal strength are averaged in the signal strength buffer and then the gain update routine is exercised every time the slow ISR is called (6.55 mSec in the preferred embodiment). A pointer is kept to check if the signal strength buffer is wrapping around. Also an additional pointer is used to keep an index of the processed values.

Pulse interval detection is implemented via a data buffer that contains values of the timestamp of each value is inspected by the pulse interval detection routine. The data buffer may overrun due to excessive noise, and the buffer has been chosen large enough that continuous pulses timestamps can be written away, as there is a small inter-pulse blanking timer active to reduce the number of detected pulses.

A pointer indicating the last processed pulse is needed to let the detection algorithm start at the not processed pulses. The detection algorithm calculates the interval between pulses in timer tics and converts these to implant crystal clock tics by division using repeated subtraction.

The start of a frame is then detected by inspecting the time differences between pulses. If a pulse interval of the frame start is detected, the algorithm checks this time position with the previous start of frame detection, to check the frame length.

The exact position of the frame is then calculated by interpolation between the beginning and end of frame positions. Accordingly, the noise in the position or jitter is reduced.

The routine searches the next start of frame pulse distance and calculates the position of the pulses inside the frame. The routine only processes whole frames. The 6.55 mSec time may contain at least 2 frames. A pointer keeps track of the processed pulses and monitors the wrapping of the pulse and gain value buffer.

Frame decoding and mass storage is implemented via the pulses inside the frame are decoded and a 16-bit word containing 8 bits of data and 8 bits of type data (error signals, data types, mode bits) are written away in a large memory buffer. Once the memory buffer is full, a secondary buffer is addressed to write away data and the storage write routine is started to empty the first data buffer into a mass storage device. At a frame rate of 500 Hz very 2 seconds a mass storage write is needed for a 1 Kword buffer size.

A further additional embodiment of multimode programmer system 5 as shown in FIGS. 5 and 6 above would include the use of the telemetry antenna 32 and DSP 42 to allow the recharging of a rechargeable battery 38 in a battery powered system. The full control of the coil switches (114 and 116 of FIG. 11A) allows the software to control battery recharging. The charging is accomplished by using the telemetry coil to receive a magnetic field at the frequency of the tuned antenna 102. The software detects the system basic frequency and adjusts the timer to drive the switches for synchronous rectification. The DSP's ADC is used for battery voltage monitoring and charge control.

The motor controller DSP based programmer of the present invention can eliminate the need for multiple programmers for telemetric communication with different medical devices. A multi-mode programmer of the present invention can be used to communicate with a plurality of different medical devices on a selective basis providing a universal programmer to minimize the programmers required to interrogate and program implantable devices from several manufacturers.

In addition, the invention may find useful application as an interrogator in emergency (first responder and emergency room) scenarios by facilitating the ability to identify and communicate with medical devices used by a given patient. In that case, the ability to obtain diagnostic and therapeutic information from a given medical device without requiring knowledge of the make and model of the device may save valuable time, possibly saving lives. In this embodiment, the programming of all parameters may not be available but universal safety modes may be programmed (such as emergency VVI). The interrogator of the present invention would downlink a command to the implanted device to cause an uplink telemetry transmission that would include the manufacturer, device model number, serial number, device status, diagnostic data, programmable parameters and contact information, if present.

A number of embodiments and features of a programmer have been described. The programmer may take a variety of forms and mechanical configurations in addition to those described herein. Moreover, the techniques described herein may be implemented in a programmer in hardware, software, firmware, or any combination thereof. If implemented in software, invention may be directed to a computer readable medium comprising program code, that when executed, performs one or more of the techniques described herein. For example, the computer readable medium may comprise a random access memory (RAM), SDRAM, FLASH, or possibly a removable memory card as outlined herein. In any case, the memory stores the computer readable instructions that, when executed cause programmer 5 to carry out the techniques described herein. These and other embodiments are within the scope of the following claims.

What is claimed is:

1. A universal programmer or interrogator for communications with various types of implantable devices (IMDs) from different manufacturers including a digital signal processing (DSP) circuit, comprising:

means for receiving a data signal from any one of the IMDs; and means for modulating said data signal consistent with one of a distinct modulation mode specific to one of the IMDs, wherein the means for modulating are contained within a motor controller DSP chip.

2. The universal programmer of claim 1 further comprising:
   an antenna system;
   a receiver in operable communication with the antenna for receiving and amplifying of said data signal; and
   a transmitter for transmitting a data signal to said one of the IMDs.

3. The universal programmer of claim 1 wherein said DSP circuit includes means for conserving battery life.

4. A multi-mode programmer in proximal and remote data signal communication link with various types of medical devices and remote monitors from different manufacturers comprising:
   a single chip DSP circuit;
   a transceiver in operable electrical communication with the circuit; and
   means for modulating the data signal consistent with one of the combinations of a modulation scheme of the medical devices and the remote monitor wherein said means for modulating within the single chip DSP circuit.

5. The programmer of claim 4 wherein said medical devices include one of implantable devices and externally mounted devices.

6. The programmer of claim 4 wherein said remote monitor includes a bi-directional communication network with a hospital or clinic for long distance remote patient monitoring.

7. The programmer of claim 4 wherein said transceiver includes an antenna adapted for both far-field and near-field telemetry.

8. The programmer of claim 4 wherein said DSP circuit includes a DSP chip fully static with low power modes forming an operable electrical system in combination with support circuitry.

9. The programmer of claim 8 wherein said support circuitry includes an antenna scheme having a first and second antenna disposed concentric one with the other.

10. The programmer of claim 9 wherein said first and second antennas are co-planar.

11. The programmer of claim 4 wherein said transceiver includes means for real-time test, means for signature evaluation and means for operating various Rx/demodulation to detect and identify the type of medical device being interrogated.

12. The programmer of claim 11 wherein the programmer is one of a patch, a belt-worn pager, PDA play-in module, a laptop plug-in module, a pendant and a watch.

13. The programmer of claim 4 wherein the communication link is selected from the group consisting of: RF, IrDA, and ultra sound.

14. The programmer of claim 4 wherein the DSP circuit includes means for reducing power requirements.

15. The programmer of claim 7 wherein said antenna includes means for battery recharge input.

16. The programmer of claim 4 wherein the communication link includes an internet connection via a transponder.

* * * * *